United States Patent
Sawayama (10) Patent No.: US 6,665,503 B2
(45) Date of Patent: Dec. 16, 2003

(54) PERMEABILITY DETECTION APPARATUS, IMAGE FORMING APPARATUS OR DIGITAL COPIER USING THE SAME, TONER CONCENTRATION DETECTION APPARATUS, AND ELECTRIC CONDUCTIVITY DETECTION APPARATUS

(75) Inventor: Noboru Sawayama, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 10/108,437

(22) Filed: Mar. 29, 2002

(65) Prior Publication Data
US 2002/0154918 A1 Oct. 24, 2002

(30) Foreign Application Priority Data
Mar. 29, 2001 (JP) ........................................ 2001-096488

(51) Int. Cl.[7] ............................................... G03G 15/08
(52) U.S. Cl. .............................. 399/63; 399/30; 399/62
(58) Field of Search ............................... 399/27, 28, 29, 399/30, 61, 62, 63

(56) References Cited

U.S. PATENT DOCUMENTS

| | | |
|---|---|---|
| 4,875,079 A | 10/1989 | Bisaiji et al. |
| 4,897,693 A | 1/1990 | Sawayama |
| 5,157,440 A | 10/1992 | Sawayama |
| 5,227,842 A | 7/1993 | Hayashi et al. |
| 5,384,628 A | 1/1995 | Takami et al. |

FOREIGN PATENT DOCUMENTS

| | | |
|---|---|---|
| JP | 06-029818 | 2/1994 |
| JP | 06-289717 | 10/1994 |
| JP | 2000-131120 | 5/2000 |

*Primary Examiner*—Hoang Ngo
(74) *Attorney, Agent, or Firm*—Oblon, Spivak, McClelland, Maier & Neustadt, P.C.

(57) ABSTRACT

A permeability detection apparatus configured to stably execute a permeability detection operation for toner concentration and characterized by improved sensitivity. The permeability detection apparatus includes: a detection circuit 22; an oscillation circuit 21 that oscillates a natural frequency to drive the detection circuit; and a phase comparison circuit 23 that extracts signals at an input side of the detection circuit and an end side of the circuit element to perform phase comparison. The detection circuit 22 includes a coil L1, a capacitor C1 connected to the coil in series or in parallel, and a resistance R1 connected to the coil in series or in parallel, and a resistance R1 connected to the coil and the capacitor. The resistance R1 allows the oscillation circuit to eliminate influence from the detection circuit and to oscillate the natural frequency continuously. The coil and the capacitor form a resonant circuit, and a resonant frequency circuit is set approximately equal to the natural frequency.

15 Claims, 7 Drawing Sheets

OSCILLATION    DETECTION    PHASE COMPARISON

FIG. 5

OSCILLATION   DETECTION   PHASE COMPARISON   INTEGRATION   Imp CONVERSION

PERMEABILITY DETECTION APPARATUS, IMAGE FORMING APPARATUS OR DIGITAL COPIER USING THE SAME, TONER CONCENTRATION DETECTION APPARATUS, AND ELECTRIC CONDUCTIVITY DETECTION APPARATUS

BACKGROUND OF THE INVENTION

1. Field of the Invention

The present invention relates to a permeability detection apparatus that detects permeability detection such as toner concentration or the like on a non-contact state or to an electric conductivity detection apparatus that detects electric conductivity of an electric conductor, which is provided in a PPC (Plain Paper Copier) and an LBP (Laser Beam Printer), for example.

2. Description of the Prior Art

Generally, in an electrophotographic copier, an electrifier evenly electrifies a surface of a photosensitive drum, a static latent image is formed by performing exposure to a photosensitive body based on image information, toner is selectively adhered on the static latent image to perform development, a toner image obtained is subjected to fixation after it is transferred on a plain paper, and thus a final image is obtained.

Figure 2:
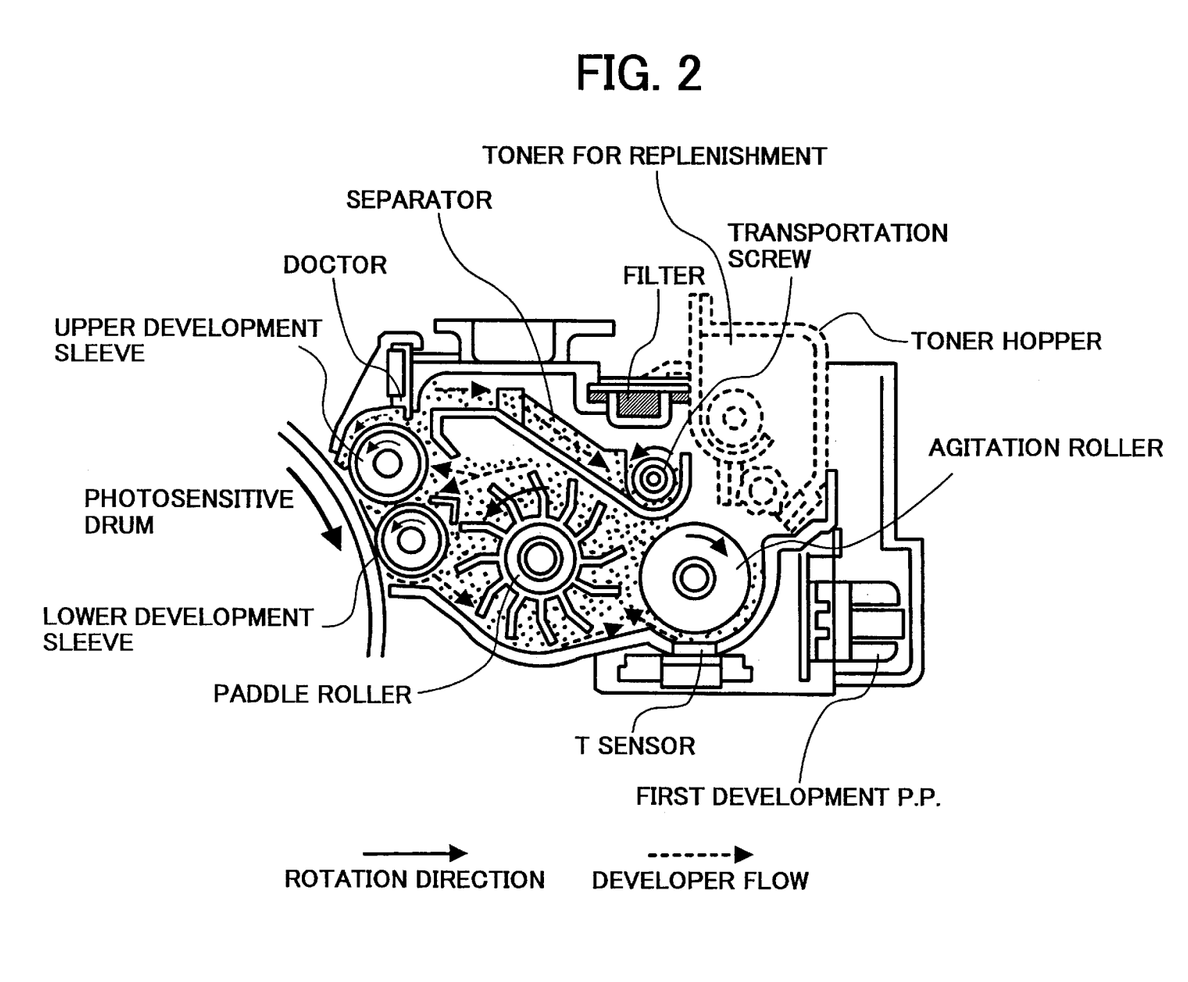
FIG. 2 is a view showing a development apparatus in which the permeability detection apparatus such as a toner concentration sensor is installed.

FIG. 2 shows a configuration example of a conventional development apparatus. The development apparatus is a two-step development roller method of a small diameter. In this method, an upper development sleeve and a lower development sleeve are disposed adjacent to the photosensitive drum, and a paddle roller supplies developer composed of non-magnetic toner, which mainly consists of coloring agent, and magnetic carrier onto the surface of photosensitive drum. Since the toner reduces although the magnetic carrier reduces little as development is executed, a toner hopper is provided to replenish the toner reduced, in which toner for replenishment is housed.

Density of a developed image becomes light when the mixture ratio of the toner to the magnetic carrier reduces, and it becomes opposite when the mixture ratio increases. To obtain an image of appropriate quality, the toner housed in the development apparatus always needs to be maintained within a constant level range, and a toner concentration detection apparatus (T sensor) for detecting toner concentration in the developer is installed for this purpose. Further, an agitation roller is provided in the development apparatus to make a mixture state of the developer and the toner for replenishment uniform.

There exists technology disclosed in Japanese Patent Laid-Open (unexamined) No. 6 (1995)-289717 as a conventional example of a concrete circuit configuration to detect the toner concentration in a development apparatus, that is, permeability. In a magnetic detection apparatus for detecting the toner concentration in this gazette, a detection coil adjacent to the developer and a reference coil remote from the developer are connected in series and driven by an alternating current drive source, a phase difference between a differential output voltage at a connection point of both coils and a voltage of the alternating current dive source is calculated, and thus detecting magnetic fluctuation in the developer. Specifically, it is the one that uses a phase difference detection of a differential transducer type.

Further, there also exists technology disclosed in Japanese Patent Laid-Open (unexamined) No. 2000-131120 as a prior art to detect with good sensitivity and stably whether or not a toner amount in the toner hopper has reduced to a reference amount. According to this technology, the development apparatus is arranged near a coil L1 and a coil L2, which are magnetically coupled with respect to each other, capacitors C1, C2 respectively connected to the coils L1, L2 in parallel are provided, the coil L1 and the capacitor C1 form a first resonant circuit, the coil L2 and the capacitor C2 form a second resonant circuit, and the two circuits constitute a tuning circuit as a whole. Then, the tuning circuit is connected to a solid-state oscillation circuit at its input side via an amplification circuit, a reference voltage that is an output of the tuning circuit and its level are compared in a comparison circuit after they are input to a wave detection circuit, and whether or not a toner level has reached the reference level is thus detected.

In this known example, when the toner level of development apparatus is approximately equal to the reference amount, a resonant frequency of the resonant circuit approximates to an oscillation frequency of the solid-state oscillator by magnetic influence of the magnetic carrier at the toner level, and thus impedance is the minimum as the tuning circuit. Furthermore, since the capacitor C1 is connected to the coil L1 in parallel to form the resonant circuit, and a Q value of the tuning circuit is set high together with the resonant circuit of the coil L1 and the capacitor C2, the toner level can be detected with high sensitivity. In the technology disclosed on the gazette, it is described that the toner amount is detected quantitatively and an analog output can be made.

In Japanese Patent Laid-Open (unexamined) No. 6 (1995)-289717 of prior art, it discloses phase difference detection by the differential transducer using the detection coil and the reference coil, which is characterized in that a resistance for sensitivity adjustment is connected to either one of the coils in parallel and toner concentration is stably controlled by gradually changing the phase of differential output voltage relative to sudden inductance change of the detection coil side.

In the technology of the gazette, a core of magnetic material in the differential transducer needs to be adjusted individually corresponding to a magnetic material detected because the both coils and the alternating current power source forms the oscillation circuit. Moreover, since it is difficult to oscillate stably, the oscillation frequency is as low as a few hundred Hz, and the coil L or the capacitor C needs to be large, there exists a problem in manufacturing in a small size and a low manufacturing cost.

Furthermore, Japanese Patent Laid-Open (unexamined) No. 2000-131120 of prior art describes that the toner concentration can be detected by using the solid-state oscillation circuit, the first resonant circuit and the second resonant circuit, and toner concentration detection is extracted as an output level of the tuning circuit that consists of the first and second resonant circuits.

As described, since changes of output amplitude in the tuning circuit are extracted as an output signal by existence/non-existence of the magnetic material (a phase difference signal is not detected), both accuracy and sensitivity are insufficient. Thus, there is a problem that analog detection of a continuous amount such as the toner concentration is difficult although existence/non-existence of the magnetic material might be possible. Moreover, although it is also disclosed that oscillation of the oscillation circuit is stabilized by allowing the amplification circuit to position between the oscillation circuit and the tuning circuit, the amplification circuit having a large number of parts needs to be specially prepared.

SUMMARY OF THE INVENTION

An object of the present invention is to provide a permeability detection apparatus in which a detection operation of permeability such as toner concentration is stably executed and the sensitivity of permeability detection is improved.

To achieve the foregoing object, a permeability detection apparatus according to one embodiment of the present invention includes: a detection circuit having a circuit element, which includes a coil arranged in a region near the magnetic material where permeability shall be detected, a capacitor connected to the coil in series or in parallel, and a resistance connected to the coil and the capacitor; an oscillation circuit that oscillates a natural frequency to drive the detection circuit; and an output circuit that extracts a signal from the detection circuit to output a permeability signal detected. The resistance has a function to allow the oscillation circuit to eliminate influence from the detection circuit and to oscillate the natural frequency continuously.

Further, a permeability detection apparatus according to another embodiment includes: the detection circuit having the circuit element, which includes the coil arranged near the magnetic material, the capacitor connected to the coil in series or in parallel, and the resistance connected to the coil and the capacitor; the oscillation circuit that oscillates the natural frequency to drive the detection circuit; and a phase comparison circuit that extracts signals from an input side of the detection circuit and an end side of the circuit element to compare the phases thereof. The resistance has the function to allow the oscillation circuit to eliminate influence from the detection circuit and to oscillate the natural frequency continuously.

Further, in the permeability detection apparatus of another embodiment, the coil and the capacitor form the resonant circuit and a resonant frequency of the resonant circuit is set approximately equal to the natural frequency.

Furthermore, a permeability detection apparatus of still another embodiment includes: a detection circuit that has a coil, which consists of a first coil of the first resonant circuit and a second coil of the second resonant circuit magnetically coupled to the first coil, first and second capacitors respectively connected to the first and second coils in series or in parallel, and a resistance connected to the first resonator circuit; the oscillation circuit that oscillates the natural frequency to drive the detection circuit; and the phase comparison circuit that extracts signals from an input side of the detection circuit and an output side of the second resonant circuit to compare the phases thereof. Resonant frequencies of the first and second resonant circuits are set approximately equal with each other and the resonant frequencies are set approximately equal to the natural frequency, and the resistance has the function to allow the oscillation circuit to eliminate influence from the detection circuit and to oscillate the natural frequency continuously.

DETAILED DESCRIPTION OF THE PREFERRED EMBODIMENTS

Figure 1:
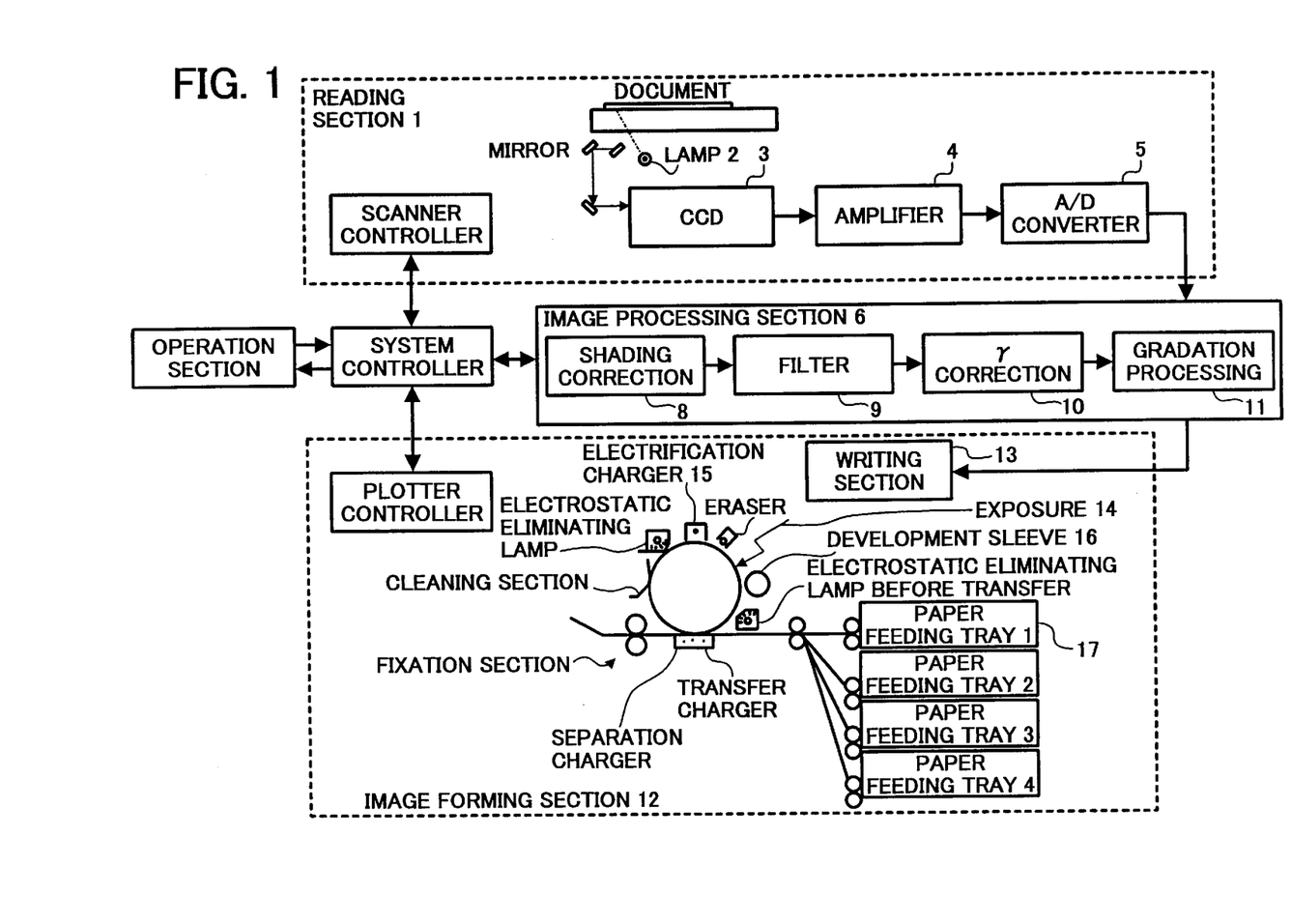
FIG. 1 is a view showing an outline regarding an electrophotographic copier to which a permeability detection apparatus according to an embodiment of the present invention is applied.

Referring to FIG. 1, an embodiment of an electrophotographic copier according to the present invention is shown. In a reading section 1 of the electro-photographic copier, light irradiated from a lamp 2 reflects on a document surface, converted into an electric signal by a CCD 3, and digital image data quantized by an A/D converter 5 is obtained after amplitude adjustment is performed in an amplifier 4. The digital image data generated is input to an image processing section 6 where shading correction processing 8, filter processing 9, $\gamma$ correction processing 10, gradation processing 11 and the like are performed in this order, and is sent to an image forming section 12.

The digital image data input to the image forming section 12 is converted into laser beam 14 in a writing section 13 in accordance with the data value thereof, the beam is irradiated on the photosensitive body electrified by an electrification charger 15, and thus forming the static latent image on a photosensitive body surface. A development sleeve 16 adheres toner on the photosensitive body according to the static latent image formed. The toner adhered on the photosensitive body is transferred on a paper sent from a paper feeding tray 17, and the paper passes through a fixation section 18 and is output as a copy document.

In the development apparatus shown in FIG. 2, the toner concentration in the development apparatus, that is, the permeability needs to be detected to maintain at a predetermined value in order to obtain a high quality image while the mixture ratio of toner relative to the magnetic carrier is always kept in an appropriate value. When reduction of toner concentration is detected, toner for replenishment is supplied from the toner hopper to control the permeability to keep the appropriate toner concentration. For this reason, the toner concentration detection apparatus (T sensor) for detecting toner concentration in the developer is installed.

Figure 3:
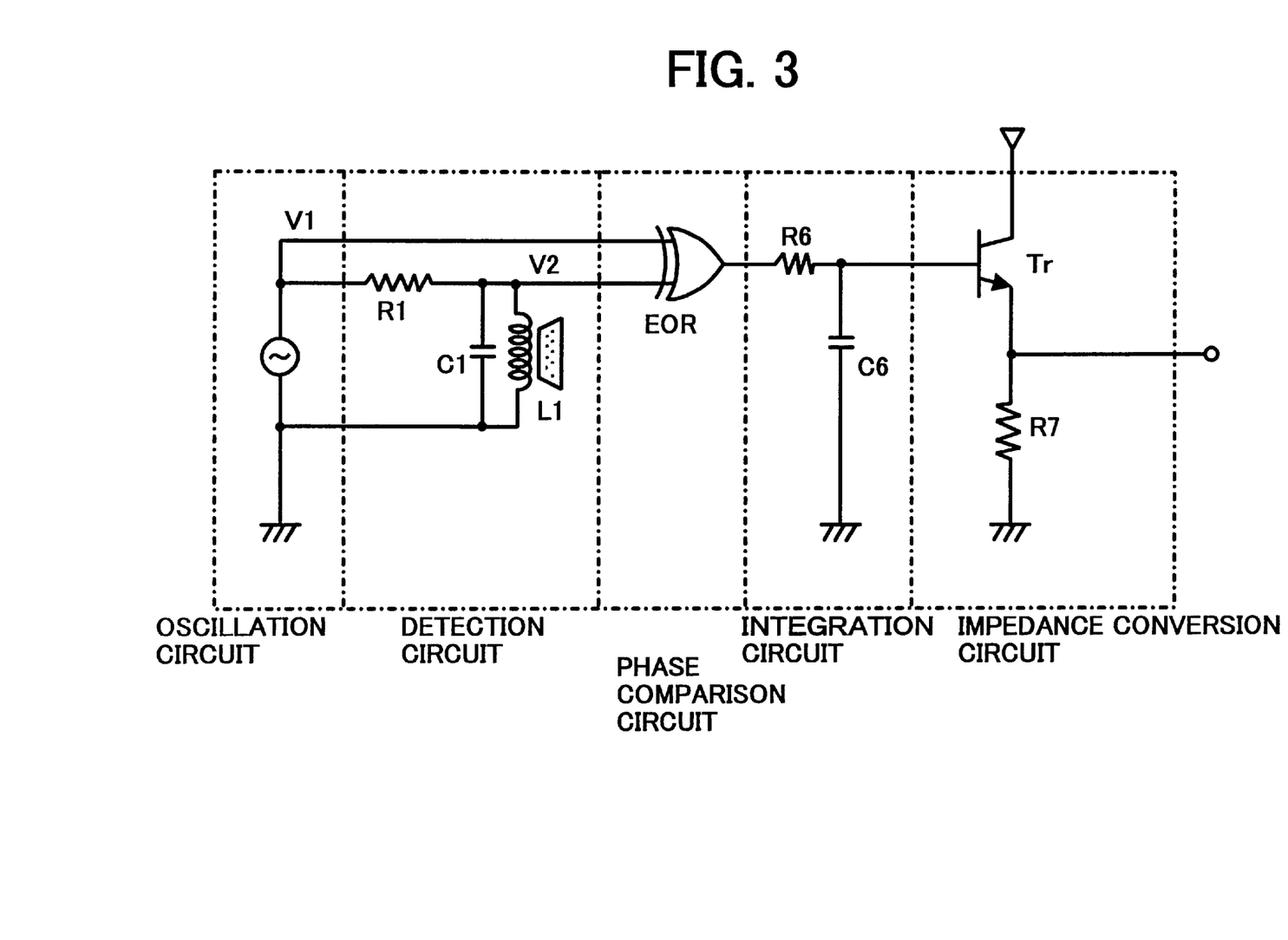
FIG. 3 is a view showing a basic circuit configuration of the permeability detection apparatus according to the embodiment.
Figure 6:
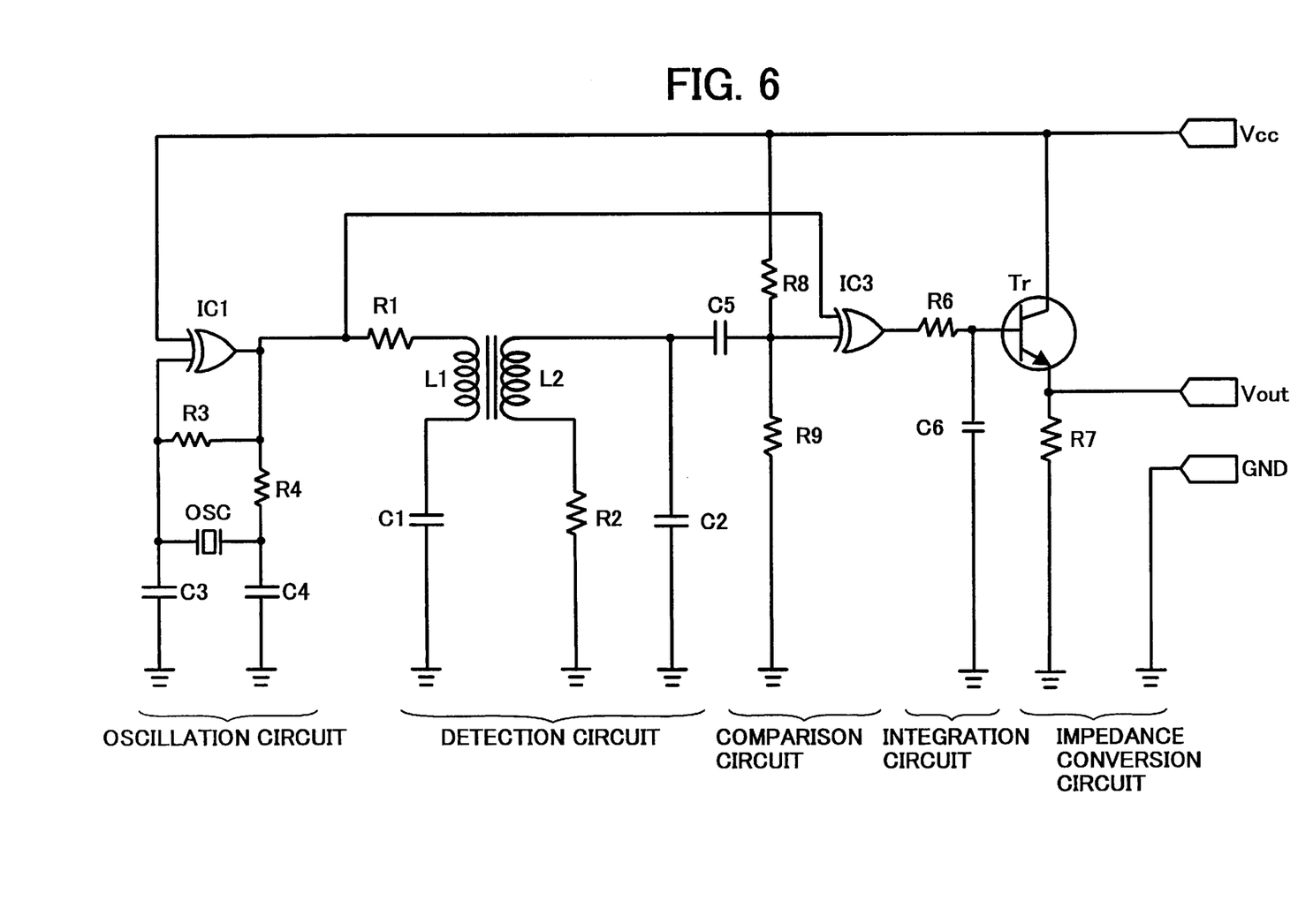
FIG. 6 is a view showing still another configuration example of the circuit configuration regarding the embodiment.

FIG. 3 shows a permeability detection circuit 20 that is a concrete example in the toner concentration detection. The permeability detection circuit 20 plainly shows the characteristic of the embodiment of the present invention, in which an oscillation circuit 21, a resonant circuit 22, a phase comparison circuit 23, an integration circuit 24, and an impedance conversion circuit 25 form a basic configuration. FIG. 6 shows the concrete circuit configuration of the oscillation circuit 21, which oscillates using a solid-state resonator such as quartz and ceramic. Since the oscillation frequency is determined based on a frequency peculiar to the solid-state resonator such as quartz and ceramic, the detection circuit is hard to be influenced by working environment of apparatus and a power source voltage, and thus stable and accurate detection is possible as a component of the permeability detection. The oscillation circuit shown in FIG. 6 may be constituted using a general-purpose logic IC.

Furthermore, the detection circuit (permeability detection circuit that substantially detects the existence/non-existence of the magnetic material and its amount) 22 is constituted of a resistance R1 to which an output from the oscillation circuit 21 is input, and the resonant circuit that consists of the coil L1 and the capacitor C1. Although the resistance R1 shall be included in the detection circuit 22 in this case, the resistance R1 may be treated as one having an isolation function, which is positioned between the oscillation circuit 21 and the detection circuit 22.

Developer 26, in which the magnetic carrier in the development apparatus and non-magnetic toner are mixed, is arranged near the coil L1 in a non-contact state, and the existence/non-existence of the magnetic material in the developer, its amount, or the toner concentration in the concrete, influences substantial inductance of the coil L1.

Since the resistance R1 inserted between an output end of the oscillation circuit 21 and the resonant circuit (L1, C1), which is a characteristic of this embodiment, can make input impedance at a resonant point of the resonant circuit large, the oscillation circuit can stably oscillate on its own circuit component. The oscillation circuit is influenced by circuit component of the resonant circuit if the resistance R1 is not inserted, and a phenomenon occurs that oscillation does not continue due to oscillation stop or the like. For this reason, the resistance R1 is not only a resistor but also may be the circuit element with a large resistance component. Incidentally, in the prior art shown in Japanese Patent Laid-Open (unexamined) No. 2000-131120, the amplification circuit is provided between the oscillation circuit and the resonant circuit, which forms a large-scale component. In FIG. 3, the oscillation circuit 21, the resistance R1, the coil L1, and the capacitor C1 constitute a closed circuit, where the resistance R1 works as the isolation function.

An output of the detection circuit 22 is extracted as the phase difference. In the concrete configuration shown in FIG. 3, an output V1 of the oscillation circuit 21 and an output V2 of the resistance R1 on the resonant circuit side (in other words, signals at both ends of the resistance R1) are applied to each input end of an exclusive OR of the phase comparison circuit 23, and an output signal dependent on the phase difference between V1 and V2 is thus obtained. Since the reason because the phase difference can be obtained by connecting both ends of the resistance R1 to both input ends of the exclusive OR is that a current flowing in the closed circuit, which consists of an output side of the oscillation circuit 21, the resistance R1, and the resonant circuit of coil L1 and capacitor C1, is a vector quantity corresponding to impedance that consists of resistance component and reactance component, the phase difference occurs between voltages at both ends of the resistance R1. In the method of taking out the phase difference, although a signal value extracted in rather small (comparing to that of a resonant circuit (described later) that has a high Q value where the first resonant circuit and the second resonant circuit are magnetically coupled), it is stable as a signal.

Figure 4:
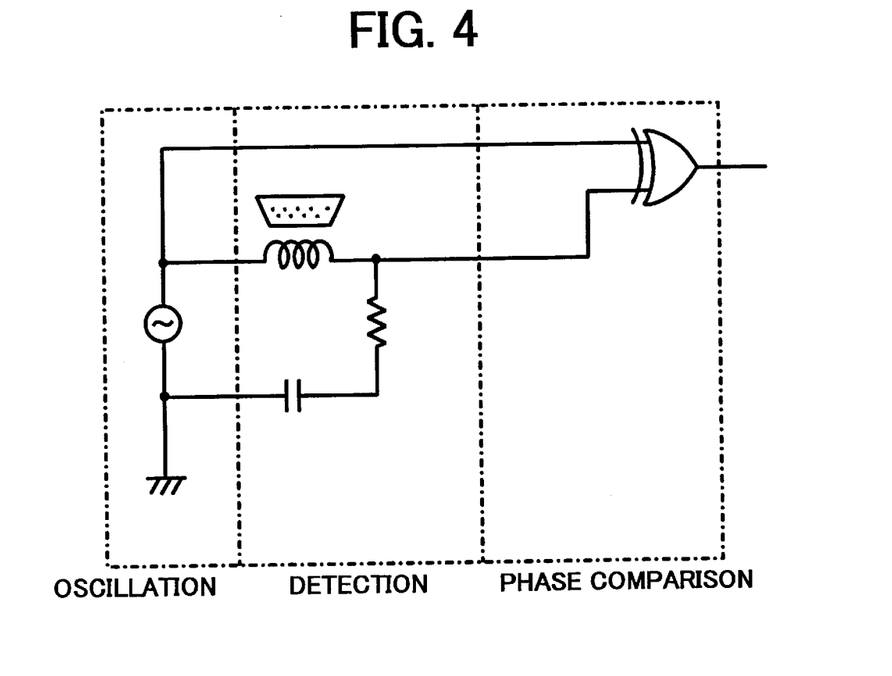
FIG. 4 is a view showing another circuit configuration of the permeability detection apparatus according to the embodiment.

Further, the configuration example shown in FIG. 4 is another circuit configuration of this embodiment. According to FIG. 4, the detection circuit is one in which a resistance is connected in series to a series resonant circuit of a coil and a capacitor, where an output of the phase difference is extracted from both ends of the coil. Even in the circuit configuration shown in FIG. 4, an equivalent circuit relative to the one in FIG. 3 is substantially constituted of components of a resistance R, a coil L, and a capacitor C. Since the resistance R works as the isolation function of the oscillation circuit and the detection circuit, and the current flowing in the equivalent circuit is the vector quantity that consists of a real number portion and an imaginary number portion, the phase difference occurs in signal component extracted from both ends of the coil.

As described, one characteristic of the embodiment of the present invention is a circuit configuration that continues stable oscillation in the oscillation circuit due to intervention of only the resistor between the resonant circuit (coil L1, capacitor C1) that performs permeability detection and the oscillation circuit 21 that drives the resonant circuit, which works as the isolation function on electrical circuits of the both circuits, and that extracts the permeability detection as the phase difference output by directly using the resistance R1 and the resonant circuit (L1, C1). In addition, according to the concrete circuit configuration shown in FIG. 3, it is one that obtains the phase difference output at both ends of the resistance R1. According to the configuration example of FIG. 3, the resistance R1 includes both the isolation function of electronic circuit in the output side of oscillation circuit and the function to extract the phase difference output of permeability detection.

Moreover, it is desirable to synchronize an oscillation frequency fosc of the oscillation circuit 21 and a resonant frequency fc of the resonant circuit (L1, C1) to extract the permeability detection output of the toner concentration or the like large. For example, the fosc and the fc are approximately synchronized in the state where the toner concentration is in an optimal value. Accordingly, a large output fluctuation value for changes of the toner concentration can be obtained (detail will be described later in the description of FIG. 7), sufficient sensitivity can be secured in the toner concentration detection.

Further, to change capacitance of the capacitor C1 shown in FIG. 3, using a configuration where a variable-capacitance diode and a direct current cutting capacitor are connected in series and a control voltage is applied to a connection point thereof via a resistance, a configuration may be adopted such that a variable capacitance is obtained by changing the control voltage.

Next, a function and an operation of the phase comparison in the phase comparison circuit 28 by an output from the detection circuit will be described using FIG. 7 and FIG. 8. In the graph shown in FIG. 7, the axis of abscissas and the axis of ordinates respectively show the frequency in the resonant circuit (L1, C1) and the phase difference between the point V1 and the point V2 shown in FIG. 3. The solid line shows a phase difference characteristic for frequency when the toner concentration is in an appropriate value, and the broken line shows a phase difference characteristic for frequency when the toner concentration is lower than the appropriate value.

Figure 7:
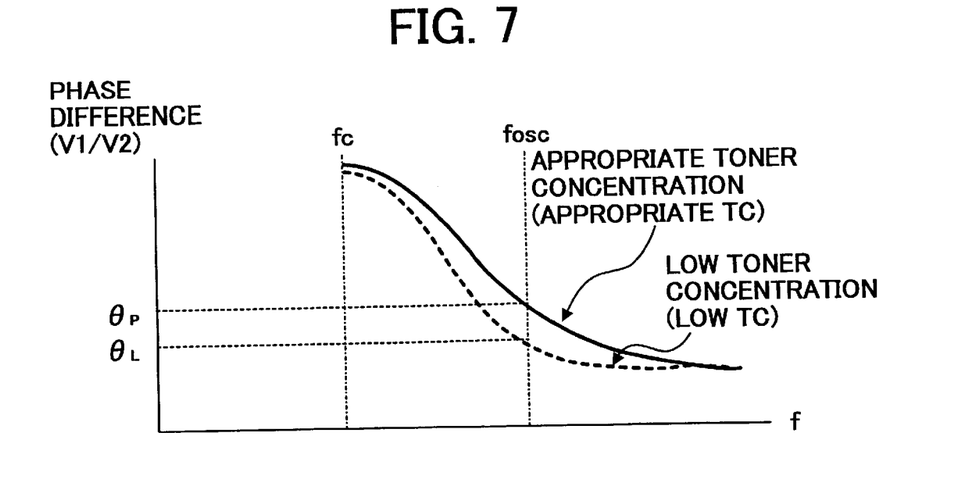
FIG. 7 is a view for explaining a basic function regarding the permeability detection apparatus according to the embodiment.

Plotting the phase difference output between V1 and V2 of the detection circuit shown in FIG. 3, characteristics of the solid line and the broken line shown in FIG. 7 (date obtained experimentally) can be obtained, in which the characteristic is shown that the phase difference output greatly fluctuate in a region where the frequency used in the detection circuit synchronizes or approximately equals to the frequency fosc of the oscillation circuit. The characteristic shows a similar tendency regardless of the level (high/low) of toner concentration. Now, in the case where the frequency synchronizes the resonant frequency fosc, the phase difference is θP degree when the toner concentration is in the appropriate value, and the phase difference is θL degree when the toner concentration is low. If the toner concentration reduces from the appropriate value, the phase difference changes from θP degree to θL degree and a sufficient output difference can be obtained.

On the contrary, in the case where the resonant frequency fc lower than the oscillation frequency fosc is used in the detection circuit 22, little phase difference output occurs between the appropriate value and a reduced value of toner concentration as it is clear from the phase difference characteristic of solid line and broken line shown in FIG. 7.

Figure 8:
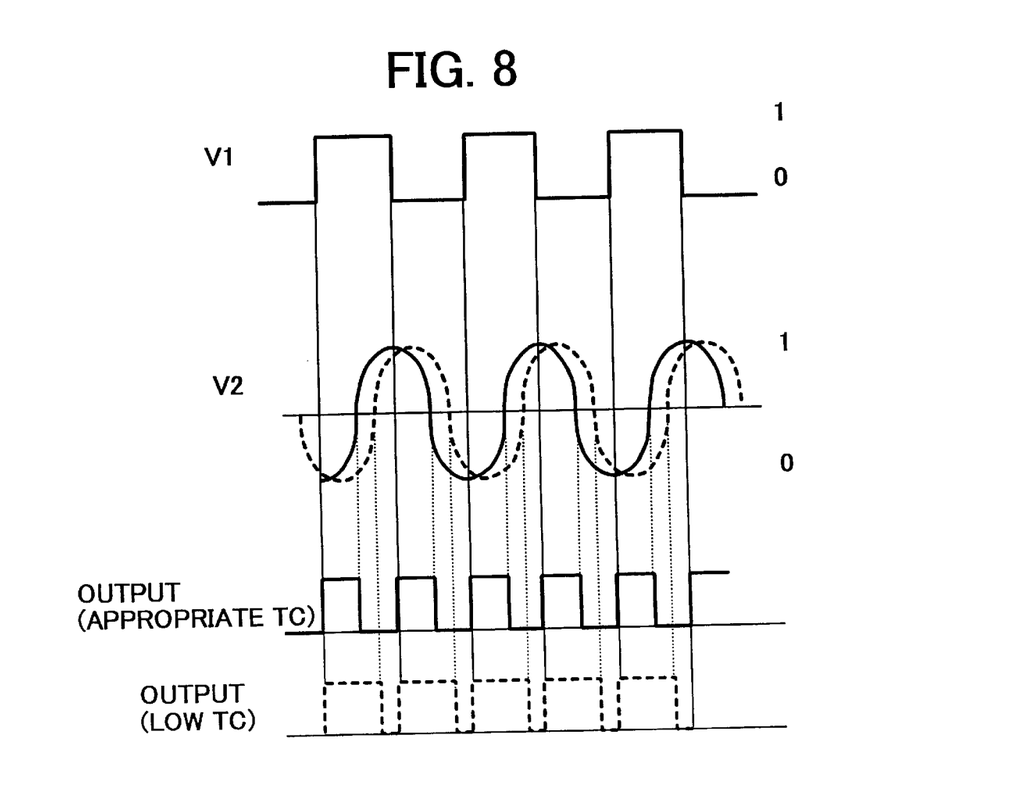
FIG. 8 is a view showing a signal waveform in the circuit configuration regarding the embodiment.
Figure 9:
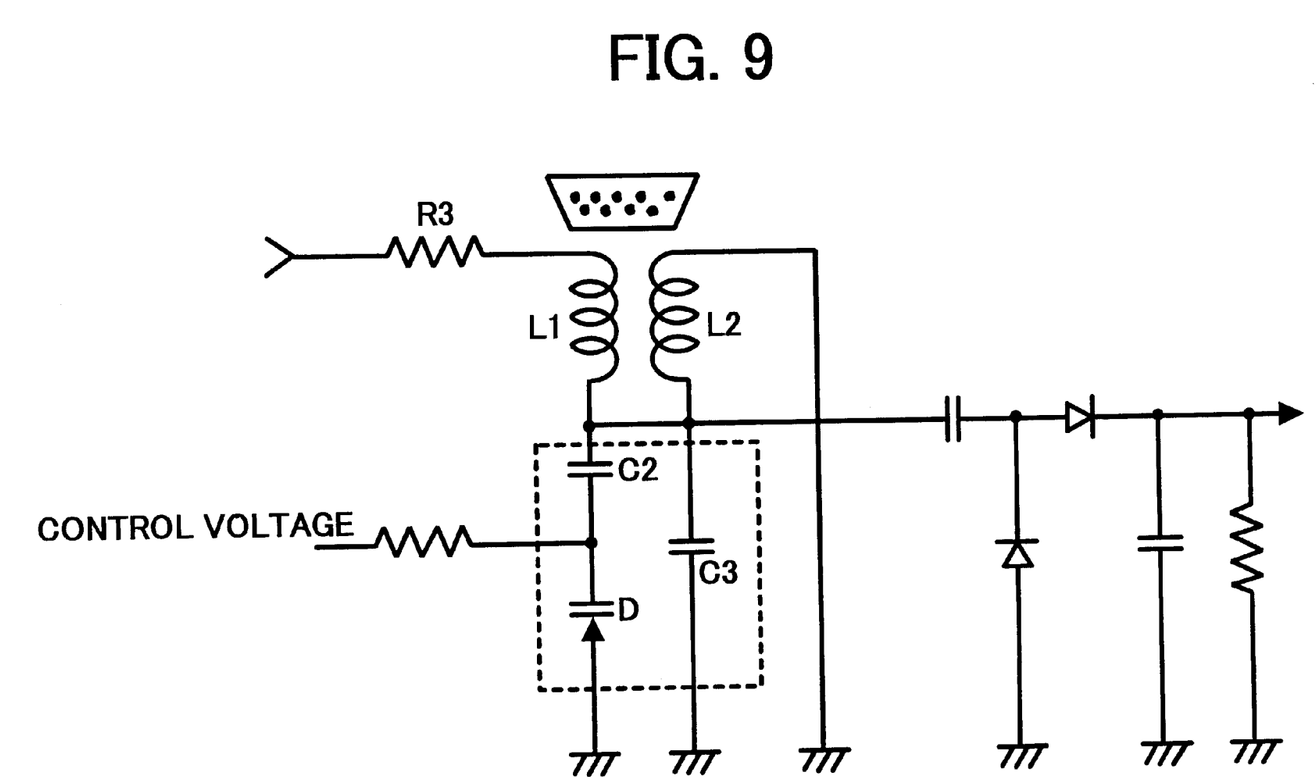
FIG. 9 is a view showing a configuration example regarding an output extraction of the permeability detection apparatus according to the embodiment.

FIG. 8 shows the output in the case where signals of V1 and V2 are applied to both input ends of the exclusive OR of phase difference comparison circuit 23. The exclusive OR with the characteristic of an output of 0 at input (0,0), (1,1) and an output of 1 at input (0,1), (1,0) is used.

Further, returning to FIG. 3, an output of the phase difference comparison circuit 23 is subject to waveform transformation processing passing through the integration circuit 24 and the impedance conversion circuit 25, and thus forming an output of the entire permeability detection circuit 20.

As described above, the embodiment having the circuit configuration shown in FIG. 3 as the concrete example is one capable of not only detecting whether or not a substance having permeability, that is, the developer containing toner and carrier for example, has reached a predetermined level in an on/off state but also detecting the continuous amount of the toner concentration or the like to output as an analog quantity. At this point, the continuous amount of the toner concentration or the like can be detected because the circuit configuration that extracts the phase difference as an output is adopted.

Furthermore, the oscillation circuit that drives the detection circuit can stably and continuously oscillate due to installation of the first resistance R1. Specifically, it is assumed that attenuating a phase change of load impedance viewed from the oscillation circuit side stabilizes oscillation. In the prior art shown in Japanese Patent Laid-Open (unexamined) No. 2000-131120, the oscillation circuit and the detection circuit (tuning circuit) are separated using the amplification circuit having high input impedance and low output impedance to prevent the oscillation of oscillation circuit from becoming unstable due to the phase fluctuation of load, but only one resistor can achieve the same effect in the foregoing embodiment of the present invention.

Figure 5:
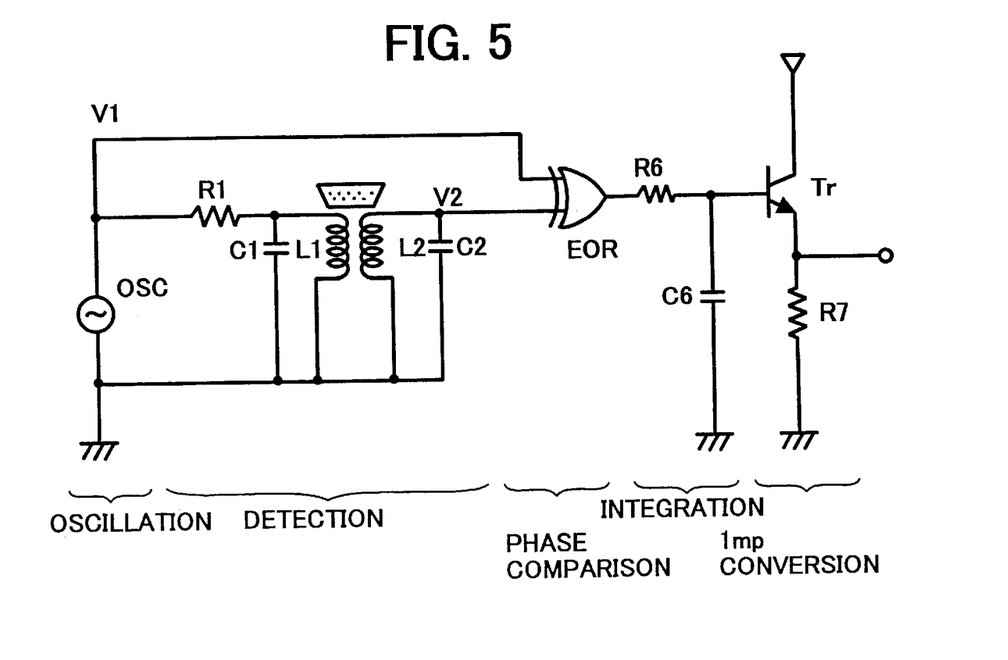
FIG. 5 is a view showing another configuration example of the circuit configuration regarding the embodiment.

Next, FIG. 5 shows another configuration example of the permeability detection circuit according to the embodiment of the present invention. The configuration example shown in FIG. 5 also includes: the oscillation circuit; the resistance R1 having the isolation function and a oscillation stabilizing function to stably continue oscillation; and a phase difference extraction section of permeability detection, which extracts the phase difference output directly using the R1 and the resonant circuit, similarly to the circuit configuration shown in FIG. 3.

In the configuration example shown in FIG. 5, a first resonant circuit that consists of the first coil L1 and the first capacitor C1 and a second resonant circuit that consists of the second coil L2 and the second capacitor C2 are provided at an output side of the resistance R1 having the oscillation stabilizing function. Herein, the first coil L1 and the second coil L2 are coupled with a magnetic coupling constant k, and the developer 26 housing the toner is arranged near the coils L1 and L2 in a non-contact state. The phase difference is extracted at a connection point of the resonant circuit and the resistance R1 and at an output point of the second resonant circuits.

According to the configuration example of FIG. 6, since resonant frequency fc1 of the first resonant circuit (L1, C1) and resonant frequency fc2 of the second resonant circuit (L2, C2) are set approximately to an equal value and the output V2 based on an integrated Q where Q1 of the first resonant circuit and Q2 of the second resonant circuit are multiplied is obtained, an accurate and sufficient phase difference output can be obtained.

Another configuration example shown in FIG. 6 is one that a second resistance R2 is inserted in a closed circuit of the second resonant circuit (L2 and C2). The reason why the second resistance R2 is provided is that since resonant frequency of the first resonant circuit and that of the second resonant circuit are set approximately to the same value and the coils L1 and L2 are strongly coupled magnetically, in driving the resonant circuit by oscillation circuit output and when its oscillation frequency is close to the resonant frequency, a secondary current proportional to a product of Q1 value of the first resonant circuit, Q2 value of the second resonant circuit, and the magnetic coupling constant k of coil flows in the second resonant circuit to greatly increase sensitivity. On the contrary, a resonant region becomes very arrow and a range of analog measurement region of permeability detection also becomes narrow, and thus it may cause an unstable operation.

As described, the Q value of second resonant circuit is appropriately adjusted by installing the second resistance R2 in the closed circuit of second resonant circuit, and a measurement range and a measurement sensitivity thus can be set to predetermined values.

The foregoing permeability detection circuit can be applied to an image forming apparatus including the development apparatus shown in FIG. 2, and can be naturally adopted to the digital copier including a printer and a scanner shown in FIG. 1.

Furthermore, in the foregoing description, the magnetic material is arranged near the first coil and the second coil in a non-contact state and changes of inductance in accordance with the permeability is utilized. But the present invention is not limited to this, but it may be the one in which a conductor is arranged in a region near the both coils and changes of inductance due to influence of a magnetic field in an eddy current in conductor by magnetic flux from the coils may be utilized. Specifically, the present invention can be also applied to electric conductivity detection of a conductor utilizing the changes of inductance in accordance with electric conductivity.

Further, although description has been made that the developer 26 is provided near the first and second coils L1, L2, it may be near either one of the coils. Still further, the circuit configuration of FIG. 3 has shown an example that output of the resonant circuit (detection circuit) is extruded as the phase difference to perform a phase comparison. However, in addition to extracting an output of the detection circuit as the phase difference, amplitude changes of either or both currents that flow in the first and second resonant circuits, which is caused by inductance changes of the first coil and the second coil due to permeability change of the magnetic material in a region near the coils, may be extracted as an output through the detection circuit (amplitude changes of a current in a single resonant circuit may be acceptable).

According to the present invention, oscillation in the oscillation circuit that drives the detection circuit of permeability can be stabilized. Further, stabilization of oscillation can be achieved by a simple circuit configuration in which one resistor is provided between the oscillation circuit and the detection circuit, which leads to cost reduction.

Furthermore, an output can be extracted at appropriate two points in the closed circuit formed by the resistance for oscillation stabilization and detection circuit in order to obtain the phase difference output, and the continuous amount of toner concentration or the like can be detected as an analog quantity.

Moreover, the resonant circuit in detection circuit adopts a configuration where it is formed of the first and second resonant circuits and the first and second coils are magnetically coupled, and sensitivity improves and detection accuracy of permeability is increased.

Still further, inserting the resistance in an LC closed circuit of the second resonant circuit can appropriately adjust the measurement range and sensitivity of permeability.

What is claimed is:

1. A permeability detection apparatus, comprising:
    a detection circuit including a circuit element which has a coil arranged in a region near a magnetic material whose permeability is to be detected, a capacitor connected to said coil in series or in parallel, and a resistance connected in series to said coil and said capacitor;
    an oscillation circuit that oscillates a natural frequency to drive said detection circuit; and
    an output circuit that extracts a signal from said detection circuit to output a permeability signal detected,
    said resistance having a function to allow said oscillation circuit to eliminate influence from said detection circuit and to oscillate said natural frequency continuously.

2. A permeability detection apparatus, comprising:
    a detection circuit including a circuit element which has a coil arranged in a region near a magnetic material whose permeability is to be detected, a capacitor connected to said coil in series or in parallel, and a resistance connected in series to said coil and said capacitor;
    an oscillation circuit that oscillates a natural frequency to drive said detection circuit; and
    a phase comparison circuit that extracts signals from an input side of said detection circuit and an end side of said circuit element to compare phases thereon
    said resistance having a function to allow said oscillation circuit to eliminate influence from said detection circuit and to oscillate said natural frequency continuously.

3. The permeability detection apparatus as claimed in claim 2, wherein
    said coil and said capacitor form a resonant circuit, and a resonant frequency of said resonant circuit is set approximately equal to said natural frequency.

4. The permeability detection apparatus as claimed in claim 3, wherein
    said resistance is connected immediately after an output side of said oscillation circuit, and signals are extracted from both ends of said resistance and input to the phase comparison circuit.

5. The permeability detection apparatus as claimed in claim 2, wherein
    said coil its connected immediately after an output side of said oscillation circuit, and signals are extracted from both ends of said coil and input to the phase comparison circuit.

6. The permeability detection apparatus as claimed in claim 1, wherein
    said oscillation circuit is constituted using a general purpose logic IC, and said oscillation circuit, said resistance, said coil, and said capacitor form a closed circuit.

7. A permeability detection apparatus, comprising:
    a detection circuit having a coil that is arranged in a region near a magnetic material whose permeability is to be detected and that essentially consists of a first coil of a first resonant circuit and a second coil of a second resonant circuit, which is magnetically coupled with said first coil, first and second capacitors respectively connected to said first and second coils in series or in parallel, and a resistance connected to said first resonant circuit;
    an oscillation circuit that oscillates a natural frequency to drive said detection circuit; and
    a phase comparison circuit that extracts signals from an input side of said detection circuit and an output side of said second resonant circuit to perform phase comparison,
    resonant frequencies of said first and second resonant circuits being set approximately to the same value and said resonant frequencies are set approximately equal to said natural frequency,
    said resistance having a function to allow said oscillation circuit to eliminate influence from said detection circuit and to oscillate said natural frequency continuously.

8. The permeability detection apparatus as claimed in claim 7, comprising:
    an output circuit that extracts any one of an amplitude change of a current, which flows in said resonant circuit, and an amplitude change of one or both of currents, which flow in said first resonant circuit and said second resonant circuit, and that outputs a permeability signal, instead of said phase comparison circuit.

9. The permeability detection apparatus as claimed in claim 1, wherein
    a circuit element having a large resistance component is provided instead of said resistance.

10. The permeability detection apparatus as claimed in claim 7, wherein
    a resistance is connected to said second resonant circuit that essentially consists of said second coil and second capacitor, and said resistance adjusts a Q value of said second resonant circuit.

11. The permeability detection apparatus as claimed in claim 7, wherein
    said oscillation circuit oscillates using a solid-state resonator that includes quartz or ceramic.

12. An image forming apparatus, wherein
    the permeability detection apparatus as claimed in any one of claims 1 to 10 is annexed to a development apparatus.

13. A digital copier, wherein
the permeability detection apparatus as claimed in any one of claims 1 to 10 is annexed to a development apparatus.

14. A toner concentration detection apparatus, wherein toner concentration of a development apparatus is detected using the permeability detection apparatus as claimed in any one of claims 1 to 10.

15. An electric conductivity detection apparatus, wherein a conductor is arranged to detect electric conductivity of said conductor instead of permeability arranged in a region near said coil in the permeability detection apparatus as claimed, in any one of claims 1 to 10.

* * * * *